(12) United States Patent
Kogure et al.

(10) Patent No.: US 7,900,523 B2
(45) Date of Patent: Mar. 8, 2011

(54) LOAD DETECTING APPARATUS AND LOAD DETECTING METHOD

(75) Inventors: Shunsuke Kogure, Toyota (JP); Mitsuhiro Ando, Toyohashi (JP); Katsuyoshi Shirai, Anjo (JP)

(73) Assignee: Aisin Seiki Kabushiki Kaisha, Kariya-Shi, Aichi (JP)

( * ) Notice: Subject to any disclaimer, the term of this patent is extended or adjusted under 35 U.S.C. 154(b) by 647 days.

(21) Appl. No.: 11/916,227

(22) PCT Filed: Jun. 16, 2006

(86) PCT No.: PCT/JP2006/312173
§ 371 (c)(1),
(2), (4) Date: Nov. 30, 2007

(87) PCT Pub. No.: WO2006/137345
PCT Pub. Date: Dec. 28, 2006

(65) Prior Publication Data
US 2010/0018327 A1  Jan. 28, 2010

(30) Foreign Application Priority Data

Jun. 21, 2005 (JP) .................................. 2005-180836

(51) Int. Cl.
*G01D 7/00* (2006.01)
(52) U.S. Cl. ............................. 73/862.041; 73/862.391
(58) Field of Classification Search ......... 73/862.041–862.046, 760, 862, 73/381–862.391
See application file for complete search history.

(56) References Cited

U.S. PATENT DOCUMENTS

| | | | | |
|---|---|---|---|---|
| 4,330,836 A | * | 5/1982 | Donofrio et al. | 702/174 |
| 5,083,467 A | * | 1/1992 | Tabota | 73/862.046 |
| 5,586,067 A | * | 12/1996 | Gross et al. | 702/139 |
| 5,642,302 A | * | 6/1997 | Dumont et al. | 700/302 |
| 5,800,480 A | * | 9/1998 | Augustine et al. | 607/96 |
| 5,993,400 A | * | 11/1999 | Rincoe et al. | 600/595 |

(Continued)

FOREIGN PATENT DOCUMENTS

JP  6-241926 A  9/1994

(Continued)

OTHER PUBLICATIONS

Form PCT/ISA/210 (International Search Report) dated Jul. 11, 2006.

(Continued)

*Primary Examiner* — Max Noori
(74) *Attorney, Agent, or Firm* — Buchanan Ingersoll & Rooney PC

(57) ABSTRACT

The present invention provides a load detecting apparatus capable of detecting load and vibration applied to a support supporting a body of a human or an animal by a load sensor provided in the support, in particular such a load detecting apparatus capable of detecting micro vibration applied to the support, with a high noise immunity.

The load detecting apparatus includes a plurality of load sensors 1 disposed in distribution within a detection target area of a support 7, a selecting means 6 for selecting one or some of the plurality of load sensor(s) 1, a detecting means 5 capable of detecting load and vibration applied to the support 7, based on the output from the selected load sensor(s) 1. The selecting means 6 effects the selection, based on either the outputs S from the respective load sensors or the outputs S from the respective load sensors, plus disposing positions of the respective load sensors.

11 Claims, 8 Drawing Sheets

U.S. PATENT DOCUMENTS

| | | | |
|---|---|---|---|
| 6,225,977 B1 * | 5/2001 | Li | 345/156 |
| 6,721,980 B1 * | 4/2004 | Price et al. | 5/713 |
| 2006/0207341 A1 | 9/2006 | Ando et al. | |
| 2007/0043508 A1 | 2/2007 | Mizota et al. | |

FOREIGN PATENT DOCUMENTS

| | | |
|---|---|---|
| JP | 2000-230853 A | 8/2000 |
| JP | 2000-258268 A | 9/2000 |
| JP | 2001-070256 A | 3/2001 |
| JP | 2001-145605 A | 5/2001 |
| JP | 2002-005761 A | 1/2002 |
| JP | 2003-209154 A | 10/2003 |
| JP | 2005-114715 A | 4/2005 |

OTHER PUBLICATIONS

Form PCT/ISA/237 (Written Opinion of the International Searching Authority) dated Jul. 11, 2006.

Office Action issued by the Japanese Patent Office in corresponding International Patent Application No. PCT/JP2006/312173 on Aug. 5, 2010 and English language translation of the Office Action.

* cited by examiner

LOAD DETECTING APPARATUS AND LOAD DETECTING METHOD

TECHNICAL FIELD

The present invention relates to a load detecting apparatus capable of detecting load and vibration applied to a support by a load sensor provided in the support for supporting a body of a human or an animal.

BACKGROUND ART

There is known a conventional load detecting apparatus for detecting load applied to a support for a load sensor, such as a bed, a mat, a seat, etc., thereby determining presence/absence of a human, an animal or a physical object. There has been also proposed an apparatus adapted for detecting micro vibrations such as heartbeat, breathing of a human, in addition to such determination of presence/absence of a human, an animal or a physical object.

Patent Document 1 identified below describes an invention relating to such load detecting apparatus. In this load detecting apparatus, a support for supporting a human body includes a vibration detecting means having a vibration generating section and a vibration detecting section disposed adjacent the vibration generating section. This load detecting apparatus further includes a vibration characteristics calculating means and a load calculating means. The vibration characteristics calculating means calculates vibration characteristics of vibration propagated due to vibration of the vibration generating section, from an output signal from the vibration detecting section. Then, the load calculating means calculates load applied to the vibration detecting means, based on an output signal from this vibration characteristics calculating means. The apparatus still further includes a human body vibration extracting section for extracting vibration component due to the human body present on the support, from the output signal of the vibration detecting section. Examples of the vibration component extracted are vibration associated with heartbeat and breathing of the human body. Finally, a human body determining means is provided for determining presence/absence of a human body on the support, based on the output signals from the human body vibration extracting section and the load calculating section.

Patent Document: Japanese Patent Application "Kokai" No. 2000-230853 (see paragraphs 8-16, FIGS. 1-5 and FIGS. 8-10).

DISCLOSURE OF THE INVENTION

Problem to be Solved by Invention

The load calculated by the load calculating section of the above-described load detecting apparatus is a load which occurs in a static manner when a human body or the like is placed on the support, i.e. a static load. On the other hand, the vibration component, such as heartbeat, detected by the human body detecting section is a micro vibration which occurs in a sporadic or intermittent manner as compared with a static load, i.e. a dynamic load. As this dynamic load is a micro vibration, its output is not so large. Then, in order to facilitate detection of the micro vibration, there is a technique to employ e.g. a piezoelectric element (see Patent Document 1) as the vibration detecting section and further to extend its sensing area. However, if the sensing area is extended, this results also in the possibility of detection of vibration not due to the human body, such as an external noise component. And, as the signal such as heartbeat is a micro vibration, there is a risk of e.g. the heartbeat being confused with such external noise component.

The present invention has been made in view of the problem described above. The object of the invention is to provide a load detecting apparatus capable of detecting load and vibration applied to a support supporting a body of a human or an animal by a load sensor provided in the support, in particular such a load detecting apparatus capable of detecting micro vibration applied to the support, with a high noise immunity.

Means to Solve the Problem

For accomplishing the above-noted object, according to the characterizing construction of a load detecting apparatus relating to the present invention, the apparatus comprises:

a plurality of load sensors disposed in distribution within a detection target area of a support for supporting a body of a human or an animal;

selecting means configured for obtaining outputs from the plurality of load sensors and subsequently selecting one or some of the plurality of load sensor(s), based on either the outputs from the respective load sensors or the outputs from the respective load sensors plus disposing positions of the respective load sensors; and detecting means capable of detecting load and vibration applied to the support, based on the output(s) from the selected load sensor(s).

According to the above-described characterizing construction, as the plurality of load sensors are disposed in distribution within a detection target area, it is possible to obtain a large sensing area for the detection of micro vibration. Further, these sensors are operable independently of each other. Therefore, by selecting one or some of them capable of detecting micro vibration effectively by the selecting means, a detection signal(s) with a high S/N ratio can be obtained. Moreover, with such selection of one or more sensors from the plurality of load sensors, there is no need for providing a further sensor dedicated to the selection of load sensors. Consequently, there arises no need for enlarging the load detecting apparatus and it is possible to obtain a compact load detecting apparatus capable of detecting micro vibration applied to a support with a high noise immunity. Further, if the selection of the load sensor(s) is effected based on the outputs from the respective load sensors and disposing positions of the respective load sensors, the selection of the load sensor(s) can be made with consideration of both the fact that the portion has the high possibility of micro vibration generation and the actual outputs of the load sensors.

Further, such load sensor capable of detecting micro vibration effectively is very likely a sensor to which a static load is being sufficiently applied as well. Therefore, according to the present characterizing construction, it is possible to provide a load detecting apparatus capable of detecting load and vibration applied to a support supporting a body of a human or an animal by a load sensor provided in the support, in particular such a load detecting apparatus capable of detecting micro vibration applied to the support, with a high noise immunity.

Preferably, the load detecting apparatus according to the present invention is characterized in that said selecting means effects the selection of one or some of the load sensor(s), based on distribution of the outputs from the load sensors relative to the disposing positions thereof.

Based on such distribution of the outputs from the load sensors relative to the disposing positions thereof in the support, it is possible to know the supported condition of the human or animal supported by the support. Therefore, the selecting means can select such load sensor(s) disposed at position(s) suitable for micro vibration detection. As a result, based on the output from the appropriately disposed load sensor(s), the detecting means can detect the micro vibration effectively.

Further, the load detecting apparatus according to the present invention is characterized in that said selecting means selects one load sensor which has the largest absolute value of the loads indicated by the outputs from the plurality of load sensors.

The load sensor showing the largest absolute load value is being subjected sufficiently to the load of a human or an animal. And, such sufficient application of the load indicates that the human or animal is placed in close and firm contact with the support. When the human or animal is placed in such close and firm contact with the support, the micro vibration can be transmitted effectively and efficiently via the support to the load sensor supported to this support. Accordingly, the micro vibration such as heartbeat can be detected with high S/N ratio. As a result, there can be obtained a load detecting apparatus capable of detecting micro vibration applied to the support, with high noise immunity.

Still further, the load detecting apparatus according to the present invention is characterized in that said selecting means effects the selection of one or some load sensor(s), based on signals having a first frequency range contained in the outputs from the plurality of load sensors and, wherein said detecting means effects the detection of the load and the vibration, based on signals having a second frequency range different from said first frequency range, also contained in the output(s) from the selected load sensor(s).

As described hereinbefore, the load detected by the load sensor includes a static load which is generated in a stable or static manner when e.g. a human body is placed on the support and a dynamic load which is generated in a more sporadic or intermittent manner in comparison with the static load. These loads differ from each other in frequencies of signals associated therewith which are generated as outputs from the respective load sensors. Therefore, by signal processing of the outputs from the load sensors in the respective different frequency ranges, the two kinds of load can be extracted separately from each other.

As described above, when the load of e.g. a human body is applied sufficiently to the support, the human body, etc. is in close and firm contact with this support, so that minor vibration such as heartbeat can be readily transmitted to the load sensor. In other words, when such static load is detected sufficiently, a dynamic load representing a minor vibration such as heartbeat can be detected easily. And, by signal processing of the outputs from the load sensors in the respective different frequency ranges of the static load and dynamic load, the two kinds of load can be detected separately from each other.

Therefore, static load will be evaluated, based on signals of a first frequency range, and a load sensor(s) will be selected based on the result of this evaluation. Then, based on a signal of a second frequency range included in the output of the selected load sensor, the dynamic load (vibration) can be detected with high noise immunity.

Further, the load detecting apparatus according to the present invention is characterized in that said selecting means effects the selection of the one or some of the load sensor(s), based on signals of a first frequency range included in the outputs of the plurality of load sensors and, wherein said detecting means effects the detection of the load and the vibration, based on a signal of a second frequency range different from said first frequency range included in the output(s) from the selected load sensor(s) and a signal of said first frequency range.

As described above, by signal-processing the outputs of the load sensors in the different frequency ranges, the static load and the dynamic load can be detected independently of each other. Further, a load sensor to which the static load is being applied sufficiently can easily detect the dynamic load representing the minor vibration such as heartbeat. Needless to say, such load sensor to which the static load is being applied sufficiently is suitable for the detection of static load also. And, the static load and the dynamic load can be detected independently of each other.

Therefore, if a load sensor is selected based on a signal of a first frequency range, for instance, the dynamic load (vibration) can be detected with high noise immunity, based on a signal of the second frequency range included in the output of the selected load sensor. Further, based on the signal of the first frequency range included in the output of the selected (sufficiently loaded) load sensor, the dynamic load can be detected with high precision.

Further, the load detecting apparatus according to the present invention is characterized in that said selecting means selects the outputs from the plurality of load sensors one after another, thereby scanning all of the plurality of load sensors present within the detection target area and subsequently selects the one or some of the plurality of load sensor(s), based on either the outputs from the respective load sensors or the outputs from the respective load sensors plus disposing positions of the respective load sensors.

With the load detecting apparatus according to the present invention, as the plurality of load sensors are disposed in distribution within the detection target area, there can be obtained a large sensing area for the detection of micro vibration. On the other hand, these load sensors are operable independently of each other. Therefore, with scanning all off these load sensors, the large sensing area can be obtained with using the independently operable load sensors.

And, the one or some load sensor(s) will be selected, based on the result of this scanning operation (either outputs from the load sensors or the outputs, plus, disposing positions thereof). Therefore, the selection of the load sensor(s) can be effected with precision, without needing to provide a further sensor dedicated to the load sensor selection.

Further, the load detecting apparatus according to the present invention is characterized in that said detecting means includes a signal processing section for signal-processing the outputs from the load sensors and an information processing section for detecting the load and the vibration based on the signal-processed outputs, and said selecting means effects selection for the scanning and the selection of the one or some of the plurality of load sensor(s), in accordance with an instruction from said information processing section.

The detecting means including the signal processing section and the information processing section is capable of detecting the load and vibration individually from the output of the load sensor. Then, based on correlation between the detection results of the respective load sensors, it is possible to select a load sensor(s) suitable for detection of the load and/or vibration of the determination target such as a human or an animal. Then, based on this determination, the load sensor(s) to be selected will be instructed. Therefore, the selecting means can select the load sensor which can detect the load and/or vibration with high precision.

Further, the load detecting apparatus according to the present invention is characterized in that said detection target area comprises an area to contact the human or animal laying or seated thereon; said plurality of load sensors comprise piezoelectric sensors for converting a strain or vibration into electric signals by the piezoelectric effect and outputting the electric signals; and said detecting means is configured to detect at least one of a weight, pulses, and breathing of the human or animal.

If an area where a human or the like is to lie down is set as the determination target area, it becomes possible to apply the present invention to a bed or the like. Similarly, if an area where a human or the like is to be seated on is set as the determination target area, it becomes possible to apply the invention to a chair, a massager chair, a seat of a vehicle, etc. Consequently, it becomes possible not only to effect the determination of whether a physical object, an animal or a human is placed or riding on such bed, chair, seat or not, based not simply on the presence/absence of load, but in a more comprehensive manner taking the micro vibration into consideration also. Further, in doing this, if the weight of the human detected from the load and pulse, breathing, etc. is detected from the micro vibration, it becomes also possible to carry out a variety of control operations according to the individual users. Moreover, checking of any abnormality and/or health check of the user too can be effected at the same time. In addition, as the piezoelectric sensors are employed as the load sensors, reduction in the electric power consumption and size reduction of the apparatus too become possible.

In the case of the above-described construction in which an area where a human or the like is to lie down or to be seated is set as the determination target area and the plurality of load sensors comprise piezoelectric sensors for converting a strain or vibration into electric signals by the piezoelectric effect and outputting the electric signals, the load detecting apparatus according to the present invention is characterized as follows.

Namely, said selecting means effects the selection of the one or some of the plurality of the load sensor(s), based on signals of the first frequency range outputted from said load sensors in response to application of the weight of the human or the animal.

Further, said detecting means detects the weight of the human or animal based on the signal of the first frequency range and also detects at least one of the pulse and breathing of the human or animal based on the signal of the second frequency range.

As described hereinbefore, by signal-processing the outputs from the load sensors in the different frequency ranges, the static load and the dynamic load can be detected independently of each other. Further, a load sensor to which the static load is being applied sufficiently can easily detect the dynamic load representing the minor vibration such as heartbeat. Needless to say, such load sensor to which the static load is being applied sufficiently is suitable for the detection of static load also. And, the static load and the dynamic load can be detected independently of each other.

Therefore, if a load sensor is selected based on a signal of a first frequency range, for instance, the dynamic load (pulse, breathing, or the like) can be detected with high noise immunity, based on a signal of the second frequency range included in the output of the selected load sensor. Further, based on the signal of the first frequency range included in the output of the selected (sufficiently loaded) load sensor, the static load (body weight) can be detected with high precision.

According to a load detecting method relating to the present invention, the method comprises the steps of:

an evaluating step of obtaining outputs one after another from a plurality of load sensors disposed in distribution within a detection target area of a support for supporting a body of a human or an animal and evaluating the outputs from the respective load sensors;

a selecting step of selecting one or some of the plurality of load sensor(s), based on either the result of evaluation at said evaluating step or on the result of evaluation at said evaluating step plus disposing positions of the respective load sensors; and a detecting step of obtaining output of the load sensor(s) selected at said selecting step and detecting one or both of load and vibration applied to the support.

Needless to say, this load detecting method too can provide the above-described functions/effects of the load detecting apparatus of the invention and can include all of the additional features thereof.

BEST MODE OF EMBODYING THE INVENTION

Preferred embodiments of the present invention will be described hereinafter based on drawings.

FIG. 1 is a block diagram showing schematically a construction of a load detecting apparatus according to an embodiment of the present invention. FIG. 2 is an explanatory view schematically showing an embodiment of installment of load sensors of the load detecting apparatus shown in FIG. 1.

As shown in the figures, the load detecting apparatus of the invention includes a plurality of load sensors 1, driving means 2 for driving these load sensors 1, a signal processing section 3 for signal-processing output signals from the load sensors 1, and an information processing section 4 for detecting load/vibration based on the signal-processed output signals. The signal processing section 3 and the information processing section 4 together constitute a detecting means 5 employed in the present invention.

In the instant embodiment, only one driving means 2 is provided for the plurality of load sensors 1. For this reason, there is also provided a selecting means 6 for selecting one of the plurality of load sensors 1 and then transmitting a driving signal D from the driving means 2 thereto. Alternatively, however, the driving signals D can always be transmitted to all of the load sensors 1, without such selection by the selecting means 6.

Further, in the instant embodiment, only one detecting means 5 is provided for the plurality of load sensors 1. For this reason, the selecting means 6 is configured to provide a further function of selecting one of the plurality of outputs from the plurality of load sensors 1 and transmitting the selected output to the signal processing section 3.

Though will be detailed later, if desired, the outputs from the respective ones of the plurality of load sensors 1 can be switched over one after another to be inputted to the signal processing section 3, thereby to scan all of the load sensors 1 present within a detection target area. Further alternatively, the selecting means 6 can be configured to transmit output(s) from a designated particular one or more of the plurality of load sensors 1 to the signal processing section 3. Further, if desired, the control of the above-described scanning operation and the designation of the load sensor(s) can be effected by the information processing section 4. In such case, it may be said that the information processing section 4 additionally provides a part of the function of the selecting means 6.

The plurality of load sensors 1 are disposed in distribution in a support 7. One preferred example of the support 7 is a seat in a vehicle such as one shown in FIG. 2. In such seat, the load sensors 1 will be disposed in e.g. its seating face 7A, and/or a backrest 7B thereof, so as to detect the weight, breathing, heartbeat of a user 10 seated therein.

Next, detection of load and vibration by the load sensors 1 will be described. FIG. 3 is a block diagram schematically showing connection of one of the plurality of load sensors 1. This figure shows the connection to one load sensor 1, separately from the other sensors, so as to facilitate explanation of detection principle of the load and vibration using the load sensors 1. FIG. 4 is a perspective view schematically showing one example of the construction of the load sensor 1 shown in FIGS. 1-3. In the instant embodiment, the load sensor 1 is configured to provide the two functions of generation of vibration and detection of vibration within a single element.

As shown in FIG. 4, referring to the construction of the load sensor 1, a piezoelectric body 13 is mounted on a substrate 11, and to upper and lower faces of this piezoelectric body 13, there are provided a first electrode 12 and a second electrode 14, respectively. To the first electrode 12, a wire 16a is electrically connected. To the second electrode 14, a wire 15b is electrically connected. Then, via the wire 15a and the wire 15b, driving signals D are provided by the driving means 2. In response to this driving signal D, there occurs a deformation in the piezoelectric body 13, which deformation causes in turn a bending deformation in the substrate 11. Conversely, when there occurs a bending deformation in the substrate 11 due to an external force, such as application thereto of a load, vibration, acceleration from the outside, this deformation causes corresponding deformation in the piezoelectric body 13. With occurrence of such deformation in the piezoelectric body 13, there is developed an electric charge due to the piezoelectric effect, thus developing a potential difference between the first electrode 12 and the second electrode 14. And, this potential difference eventually becomes a detection signal for the load, vibration, acceleration.

Incidentally, a piezoelectric substance constituting this piezoelectric body 13 can be e.g. a ceramic piezoelectric material, a high-molecular piezoelectric material such as polyvinylidene fluoride (PVDF), or a composite piezoelectric material obtained by mixing a resin such as rubber and a ceramic powder. Among these, a high-molecular piezoelectric material and the composite piezoelectric material are preferred because of their superior flexibility.

FIG. 5 is a waveform diagram schematically showing an example of the driving signal D from the driving means 2 shown in FIG. 1 and FIG. 3.

The driving means 2 periodically outputs the driving signal D as illustrated in FIG. 5, thereby to apply a driving voltage between the first electrode 12 and the second electrode 14 of the load sensor 1. In order to obtain efficient vibration of the load sensor 1, it is preferred that the frequency of the driving signal D be set equal to the resonance frequency of the piezoelectric body 13 or the load sensor 1. In general, the frequency will have a value ranging from a few kHz to a few hundreds kHz. The frequency can be optimized, depending on a desired level of load to be detected and detection precision. Further, it is possible to electrically connect the driving means 2 and the wires 15 (16a and 15b) to each other during the period when the driving signal D provides a driving voltage (the period when the signal has a positive voltage value) and to disconnect these from each other during the period when the signal D does not provide the driving voltage.

As shown in FIG. 3, the wire 15 is connected also to the signal processing section 3. The signal processing section 3 constitutes a detecting means 5 and processes the output signal (detection signal S) of the load sensor 1.

FIG. 6 is a waveform diagram schematically showing an example of an input signal to the detecting means 5 (signal processing section 3). As shown in FIG. 6, the signal processing section 3 inputs a superimposed signal R comprised of the driving signal D and the detection signal S from the load sensor 1 superposed with each other. In FIG. 6, the square-wave positive pulse signals are the driving signals D, whereas the square-wave negative half-wave signals are the detection signals S. Then, the signal processing section 3 extracts the detection signal S of the load sensor 1 from this superimposed signal R and outputs a value of load, vibration or acceleration applied to the load sensor as a voltage value.

FIG. 7 is a waveform diagram schematically showing an example of the detection signal S from the load sensor 1 extracted at the signal processing section 3. FIG. 7(a) shows an example of the waveform when e.g. no external load, vibration or acceleration is applied to the load sensor 1, that is, when the external force such as a load is small. FIG. 7(b) shows an example of the waveform when a larger load, vibration or acceleration than the case of FIG. 7(a) is applied to the load sensor 1. As shown, the greater the load, the smaller the negative amplitude of the detection signal S.

FIG. 8 is an explanatory view schematically showing the operational principle of the load detecting apparatus of the invention. As shown in FIG. 8(a), the driving signal D has a positive amplitude VD with a cycle T. With this driving signal D, during a period TD (driving period), a charge Q1 is provided to the load sensor 1, so that by the piezoelectric effect, there occurs a bending deformation in the load sensor 1 as indicated by a broken line. During a period TS (detecting period) when no positive pulse of the driving signal D is outputted), the load sensor 1 which has been bent returns to the initial condition as indicated by a solid line, in the course of which there is outputted a detection signal S having the amplitude VS of the opposite direction to that of the driving signal D. FIG. 8(a) shows a case of non-loaded condition, showing the amplitude of the voltage value V1.

The amount of the bending deformation of the load sensor 1 due to application of the driving signal D depends on he load, vibration, acceleration applied to the load sensor 1. For instance, in the case of the example shown in FIG. 8(b), the load sensor 1 is subjected to a load in the opposite direction to the direction to be bent by the driving signal D. The load sensor 1 will be bent and then become stable with balancing between the reverse load (bending force) generated by the driving signal D and the load applied thereto. The greater the load applied, the smaller the amount of bending deformation. Conversely, the smaller the load applied, the greater the amount of bending deformation. Therefore, even if the load sensor 1 is driven by the same driving signal D, the bending amount of the load sensor 1 in the case shown in FIG. 8(b) is smaller than the bending mount in the case of the non-loaded condition shown in FIG. 8(a). As a result, the amount of electric charge generated by the piezoelectric effect is also smaller and so is the amplitude of the detection signal S having the amplitude VS of the opposite direction to that of the driving signal D. In the case of the non-loaded condition shown in FIG. 8(a), the signal has the amplitude of the voltage value V1, whereas in the case of the loaded condition shown in FIG. 8(b), the signal has an amplitude of a voltage value V2.

FIG. 9 shows a graph schematically illustrating relationship between the load applied to the load sensor 1 and the amplitude value VS of the detection signal S of the load sensor 1. As shown, the amplitude value VS of the detection signal S of the load sensor 1 exhibits a tendency of progressively decreasing with increase in the load.

Incidentally, in case only the vibration or acceleration applied to the load sensor 1 is to be detected, the function of the driving means 2 can be stopped, so that the signal processing section 3 effects the signal processing of the detection signal S from the load sensor 1.

Further, in case the load, vibration and acceleration are applied at one time to the load sensor, there will be outputted a composite waveform depending on the load, vibration and acceleration. By decomposing such composite waveform at the signal processing section 3, the load, vibration and acceleration can be detected at one time.

FIG. 10 shows a waveform diagram schematically showing input signals to the detecting means 5 (signal processing section 3) in such case when the load, vibration and acceleration are applied at one time to the load sensor 1. FIG. 10(a) show a waveform of a superimposed signal R comprised of the driving signal D and the detection signal S of applied static load superimposed each other. FIG. 10(b) shows a waveform of a superimposed signal R comprised of superimposing the above superimposed signal R further with a detection signal S in the case of application of a dynamic load. In this, the static load represents a load of e.g. a body weight of a human, whereas the dynamic load represents vibration due to heartbeat or breathing of the human. In this case, as described hereinbefore, the frequency of the driving signal D can have a value ranging from a few kHz to a few hundreds kHz. In the instant embodiment, the frequency ranges from one hundred to a few hundreds kHz. The vibration due to heartbeat of a human has a frequency of 5 Hz approximately. The vibration due to breathing of a human has a frequency ranging from 0.1 Hz to 1 Hz approximately. Therefore, as shown in FIGS. 10(b) and (c), the vibrations due to heartbeat and breathing will show as pulsation P by a cycle TV longer than the cycle of the driving signal D, in the detection signal S and superimposed signal R.

At the signal processing section 3, based on such difference in the frequency components, the static load and the dynamic load are separated from the superimposed signal R. FIG. 11 is a block diagram schematically showing an exemplary construction of the signal processing section 3. As shown, the signal processing section 3 includes a low-frequency signal processing circuit 31, a high-frequency signal processing circuit 32 and a signal processing circuit 33.

The low-signal processing circuit 31 incorporates a low-pass filter (LPF) having an upper limit frequency ranging from 10 to 100 Hz approximately. The waveform shown in FIG. 10(c) is an example of the waveform obtained after processing at this low-frequency signal processing circuit 31. As shown, the pulsation component due to heartbeat or breathing alone is extracted.

The high-frequency signal processing circuit 32 incorporates a band pass filter (BPH) having the frequency of the driving signal D as its mean frequency, for the purpose of separation of the detection signal S of the static load in cooperation with the driving signal D. And, as described above with reference to FIGS. 6 through 8, the static load will be detected based on the amplitude value. Then, based on the signals having been subjected to the signal processing at the low-frequency signal processing circuit 31 and the high-frequency signal processing circuit 32, the signal processing circuit 33 determines the frequency and magnitude of the pulsation indicative of the vibration and the magnitude of the amplitude value indicative of the static load.

The information processing section 4 constituting the detecting means 5 stores therein basic data concerning correlation between actually determined values and values associated with detection target events such as the heartbeat, breathing and body weight. Some examples of such correlations are a correlation between the voltage amplitude value VS of the static load and the load (see FIG. 9), and a correlation between the frequency of the dynamic load and the heartbeat. Then, the information processing section 4 calculates numeric values of e.g. heartbeat, breathing and body weight, based on the value determined at the signal processing section 3.

The foregoing description concerns signal processing for one load sensor 1 based on FIG. 3. However, the inventive load detecting apparatus actually includes a plurality of load sensors 1 as shown in FIG. 1. Hence, with reference to a flowchart shown in FIG. 12, there will be described next a processing procedure by the inventive load detecting apparatus having the plurality of load sensors 1.

A load detecting method using the load detecting apparatus includes at least three steps, i.e. an evaluating step, a selecting step and a detecting step. The evaluating steps is a step of obtaining outputs one after another from the plurality of load sensors 1 disposed in distribution within a detection target area of the support 7 and evaluating the outputs from the respective load sensors 1. The selecting step is a step of selecting one or some of the plurality of load sensors 1, based on the result of evaluation at the evaluating step or based on the result of evaluation at the evaluating step, plus the disposing positions of the respective load sensors 1. The detecting step is a step of obtaining output of the load sensor(s) 1 selected at the selecting step and detecting one or both of load and vibration applied to the support 7.

Upon start of the procedure, first, a variable (i) is set to zero and a variable (j) is initialized to a total number (n) of the load sensors 1 (step #0). The plurality of load sensors 1 included in the support 7 are given a plurality (n units) of respective serial sensor numbers No. 0 to (n-1). Then, in accordance with these sensor numbers (No.) thereof, the output (detection signals S, superimposed signals R) of the load sensor 1 is obtained and signal-processed (step #1) and the result thereof is stored (step #2). Upon completion of signal processing for one load sensor 1, the variable (i) is incremented (step #3). And, the foregoing process from #1 to #4 is repeated until matching between the incremented variable (i) and the variable (j) is confirmed. The above-described steps from #1 to #4 correspond to the "evaluating step" in the inventive method. And, at this evaluating step, all of the load sensors 1 supported to the support 7 are to be scanned.

Incidentally, at this evaluating step, it will suffice to effect the signal processing by only either one of the low-frequency signal processing circuit 31 and the high-frequency signal processing circuit 33 of the signal processing section 3 described above. That is, it will suffice for the information processing section 4 to effect the calculation required for the selection of the load sensor(s) 1, based on the result of signal processing by either one of the circuits. Therefore, the processing time at the information processing section 4 can be restricted advantageously. For instance, at the evaluating step, with using the high-frequency signal processing circuit 32, loads indicated by the outputs from the plurality of respective load sensors 1 will be evaluated in the first frequency range (high frequency range). In this, it is not absolutely needed for the information processing section 4 to effect the load calculation with high precision. Instead, it will suffice if the loads indicated by the respective load sensors 1 can be compared with each other.

In succession, the process determine the serial sensor number (NO.) of the load sensor 1 to be used for the actual detections of the static and dynamic loads (step #5). This corresponds to the "selecting step" in the inventive method. The selecting means 6 shown in FIG. 1 includes a function of a demultiplexer as well as a function of a multiplexer. The demultiplexer function is a function of distributing the driving signals D from the driving means 2 to the respective load sensors 1. The multiplexer function is a function of selecting the output signal from each load sensor 1 and transmitting the selected signal to the detecting means 5. The selecting means 6 transmits the driving signal D to the load sensor 1 determined at the selecting step and then transmitting the detection signal S (superimposed signal R) from this load sensor 1 to the detecting means 5. The load sensor 1 to be selected can be either one sensor or a plurality of sensors. That is, one or some load sensors is/are selected from the plurality of load sensors 1.

In the above, according to one embodiment of the invention, the selecting means 6 selects a load sensor 1 which has the largest absolute value of the load indicated by the outputs of the plurality of load sensors 1. Such load sensor 1 having the largest absolute value of load is the sensor to which the load of a human or animal is being applied sufficiently. And, the sufficient application of load means that the human or animal is placed in close and firm contact with the support 7. Micro vibration such as heartbeat can be detected with high S/N ratio when the vibration is transmitted effectively to the support 7 and the load sensor 1 provided in the support 7. As a result, it is possible to obtain a load detecting apparatus capable of detecting micro vibration applied to the support 7, with high noise immunity.

Next, based on the detection signal S from the selected load sensor 1, the detecting means 5 effects the signal processing and information processing described above (step #5) and then outputs the result of detection (step #6). These steps #5 and #6 correspond to the "detecting step" in the inventive method.

One example thereof has been described above in which the loads indicated by the respective outputs of the plurality of load sensors 1 are evaluated in the first frequency range (high frequency range). In this case, at the detecting step, the detecting means 5 detects the load and vibration, based on the output of the selected load sensor 1, in the first frequency range and in the second frequency range (low frequency range) different from the first frequency range. More particularly, at the detecting step, the load and the vibration are detected, with using both the low-frequency signal processing circuit 31 and the high-frequency signal processing circuit 32.

Further, preferably, the selecting means 6 effects the selection, based on the distribution of outputs from the plurality of load sensors 1, relative to the arrangement of these load sensors 1 on the support 7. FIG. 13 is an explanatory view showing an example of a load sensor 1 to be selected. FIG. 13 shows a seating face 7A of a seat as the support 7 shown in FIG. 2, as seen along an upper direction of the seating face 7A (the direction of the head of the user) when a user 10 is seated on the seating face 7A. In this figure, for facilitating the explanation, feet 10A and 10B of the user 10 are shown.

In this case, the load sensors 1 located under the hip and the thighs of the user 10 detect relatively large static loads. Therefore, by observing the distribution of the static loads of all of the load sensors 1 relative to the disposing positions of all of the load sensors 1, the selecting means 6 can estimate the positions of the hip and thighs on the seating face 7A. This estimation includes the case when the estimation is effected by the information processing section 4 capable of functioning as a portion of the selecting means 6. And, for determination of heartbeat from the veins in the thighs, the selecting means 6 can select load sensors 1A and 1B which are located under the thighs.

If the above process is effected similarly for the backrest 7B, a load sensor(s) 1 corresponding to the positions of lungs, the heart, etc. can be selected, so that the breathing, heartbeat, or the like can be detected effectively. Further, with respect to determination of the body weight of the user 10, a load sensor (s) 1 located under the hip can be employed. Alternatively, the method can use those load sensors 1 which are located in distribution under the hip and the thighs. In these manners, different sensors can be selected, in accordance with the target of detection.

Incidentally, as a specific embodiment of the block diagram shown in FIG. 1, it is conceivable to construct the selecting means 6 from an analog multiplexer or analog demultiplexer, the signal processing section 3 from an analog signal processing circuit including a filter circuit or the like, the information processing section 4 from an arithmetic logic circuit including an A/D converter, a logic circuit, and a microcomputer, and the driving means 2 from a pulse generating circuit, a microcomputer or the like.

And in the case of such construction, the selection of the load sensor(s) 1 at the evaluating step and detecting step is effected often by an operation of the multiplexer or demultiplexer according to a selection instructing signal from a microcomputer. Therefore, in this case, it can be said that the microcomputer functions also as the selecting means 6. Further, in case the driving means 2 comprises a microcomputer, this can be the same microcomputer functioning as the information processing section 4 and/or the selecting means 6. Namely, the respective sections shown in FIG. 1 are sections represented in terms of their functions, not representing any physically independent elements and/or circuits in an embodiment.

The load detecting apparatus according to the present invention can be applied to a bed, a chair, a seat of a vehicle, a massage chair, etc. In the case of such applications, the load sensors 1 should be disposed at positions near the user, e.g. under the outer surface of the seating face. Further, the load sensors 1 can be arranged in the form of matrix on a flexible base so that the sensors 1 can be incorporated within a mat, thereby facilitating transport and installment thereof. And, if the sensors are used simultaneously with e.g. a sofa, a sleeping mat, a seating mat, etc., the pulse, breathing etc., can be determined while the user is relaxing. The determined information can be utilized for maintenance of body condition, discrimination of the different users from each other, etc. In the case of maintenance of body condition, the information can be utilized for health control of a solitary living person, detection of abnormality, etc. In the case of discrimination among different users, the information can be utilized for determination of use or non-use of a vehicle safety device (airbag, a seat belt, etc.) or setting of appropriate providing condition, etc.

In the case of the application to a vehicle seat, during vehicle run, the vibrating noise and electric noise will increase, compared with the cases of engine stop and vehicle stop. According to the present invention, however, from the plurality of load sensors 1, a load sensor 1 suited for micro vibration detection is selected. As a result, even under such noise-full situation, the micro vibration can be detected effectively, with using a signal having a high S/N ratio.

As described above, the present invention has provided a load detecting apparatus capable of detecting a load and vibration applied to a support 7 by means of load sensors 1 provided in the support 7, and in particular, a load detecting apparatus capable of detecting micro vibration applied to the support 7, with high noise immunity.

INDUSTRIAL APPLICABILITY

The load detecting apparatus according to the present invention can be applied to a bed, a chair, a vehicle seat, a massage chair, etc.

Figure 1:
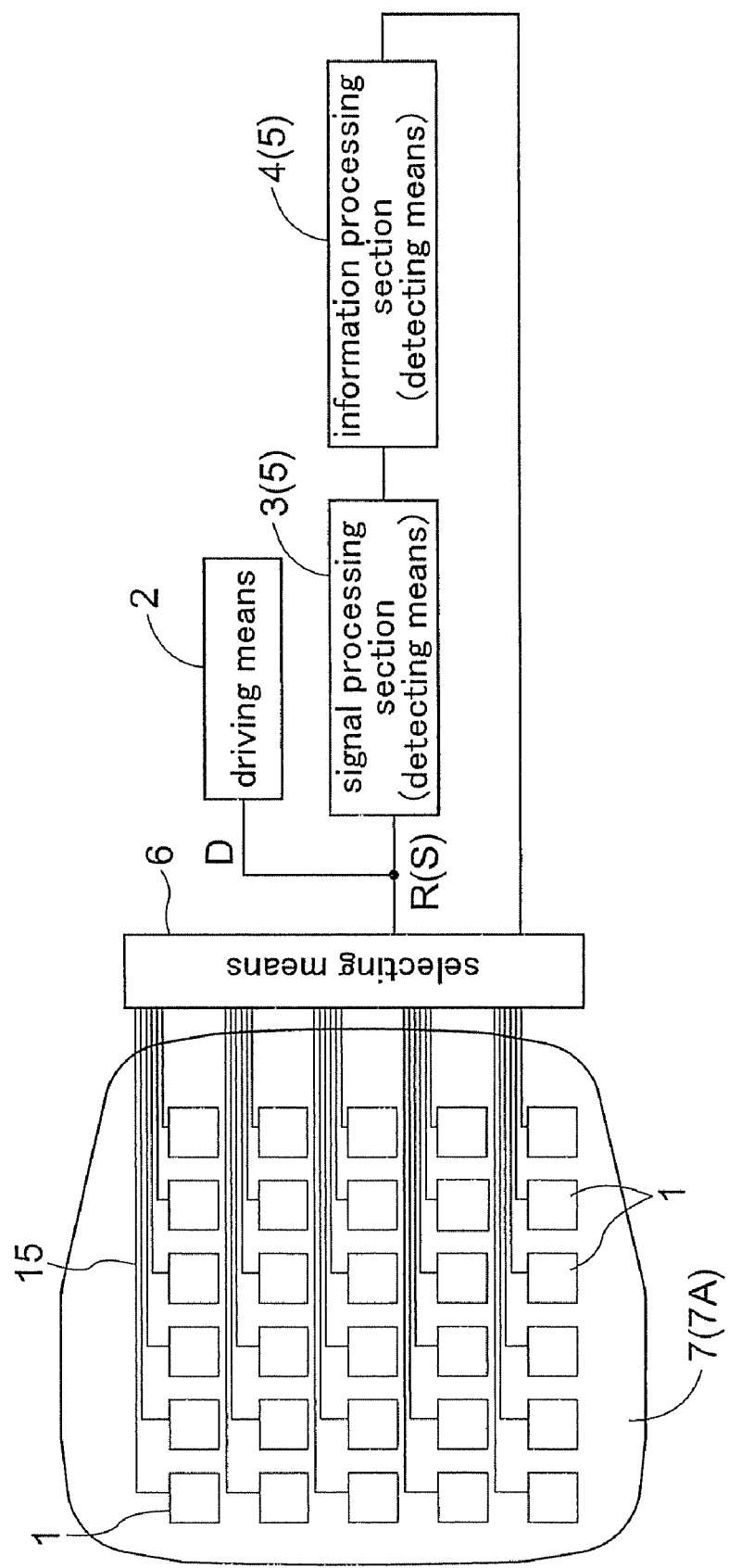
[FIG. 1] a block diagram schematically showing a construction of a load detecting apparatus according to one embodiment of the present invention.
Figure 2:
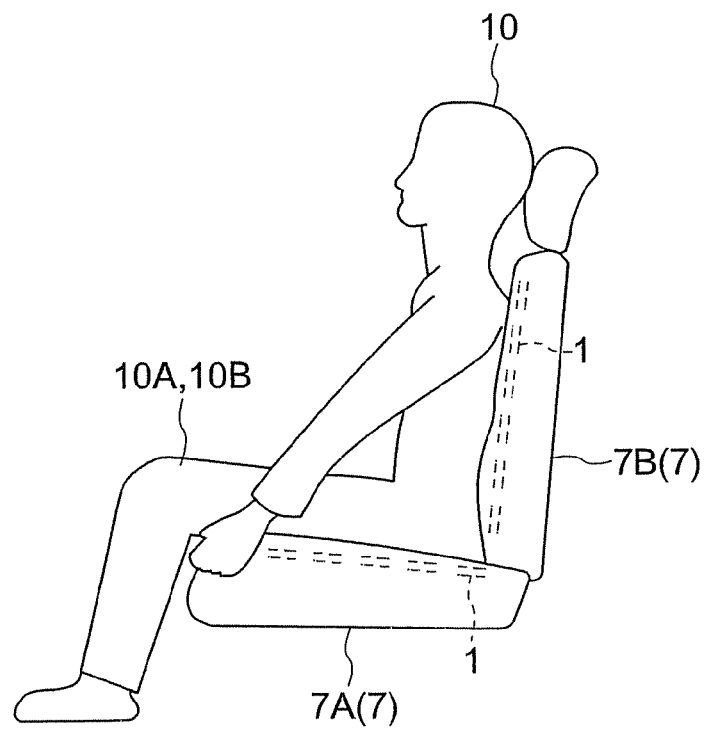
[FIG. 2] an explanatory view schematically showing an example of embodiment of arrangement of the load sensors of the load detecting apparatus shown in FIG. 1.
Figure 3:
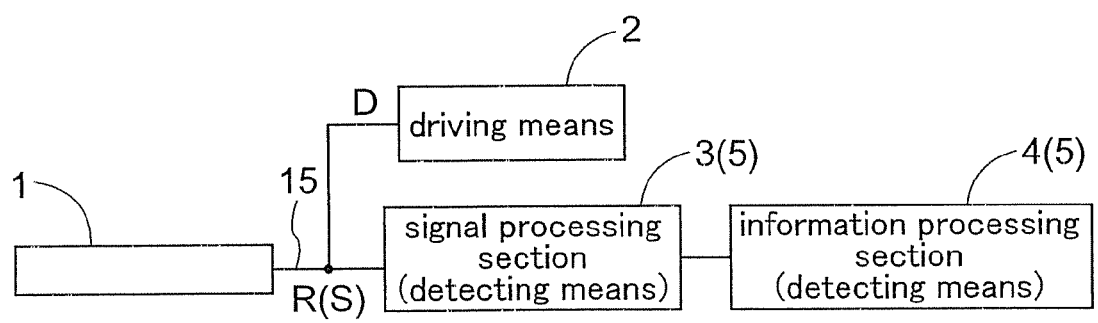
[FIG. 3] a block diagram schematically showing connection of one load sensors among the plurality of load sensors shown in FIG. 1.
Figure 4:
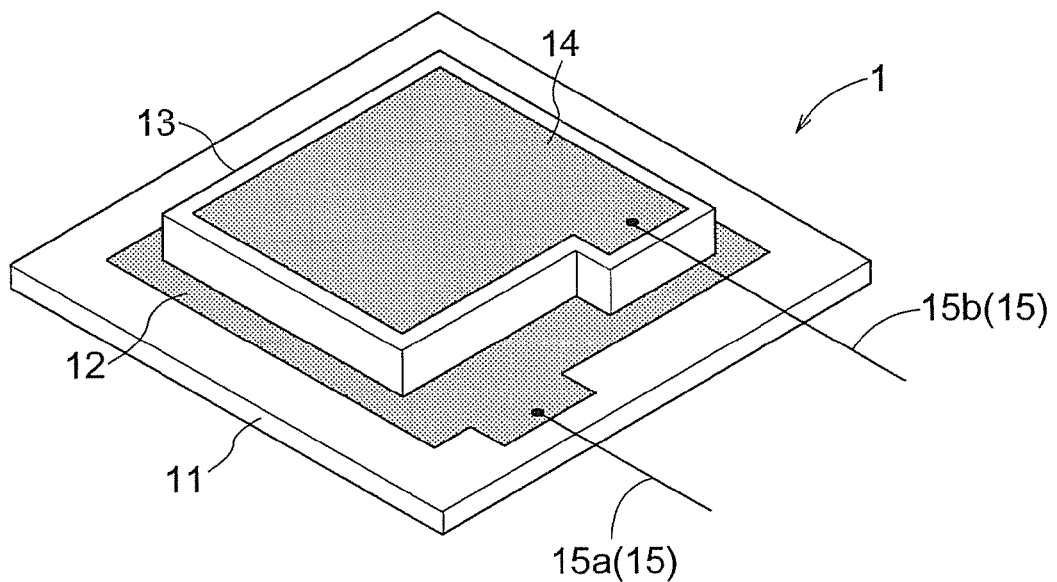
[FIG. 4] a perspective view schematically showing an example of construction of the load sensors shown in FIGS. 1-3.
Figure 5:
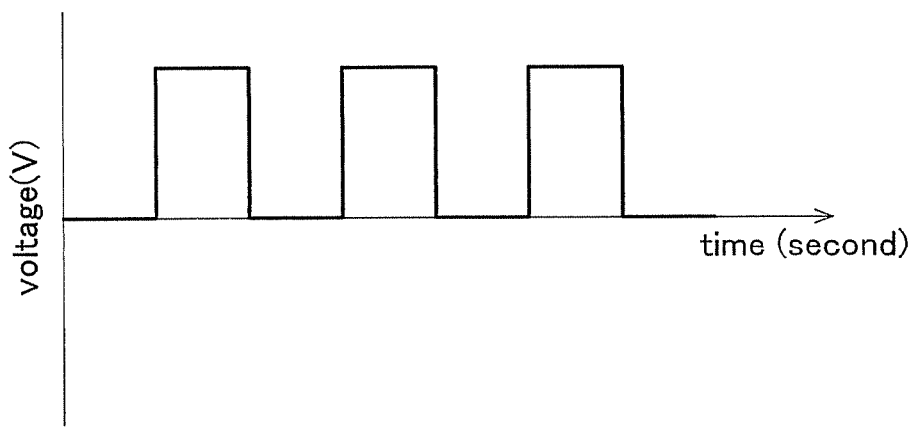
[FIG. 5] a waveform diagram schematically showing an example of a driving signal from driving means shown in FIGS. 1-3.
Figure 6:
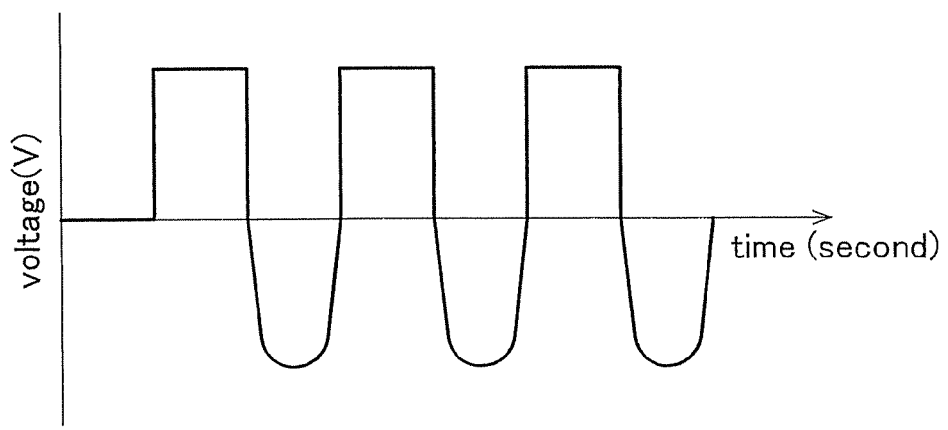
[FIG. 6] a waveform diagram schematically showing an example of input signal to detecting means shown in FIGS. 1-3.
Figure 7:
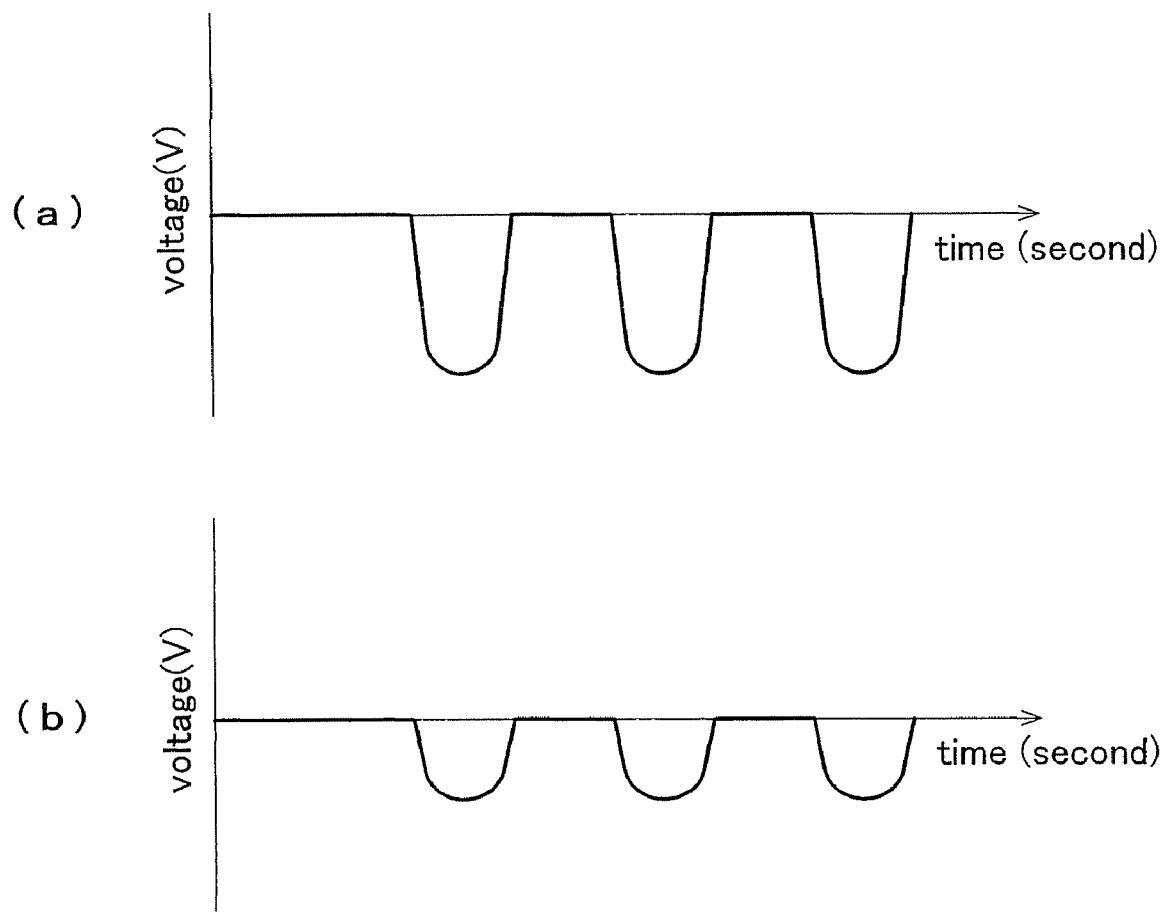
[FIG. 7] a waveform diagram schematically showing an example of a detection signal from a selected load sensor.
Figure 8:
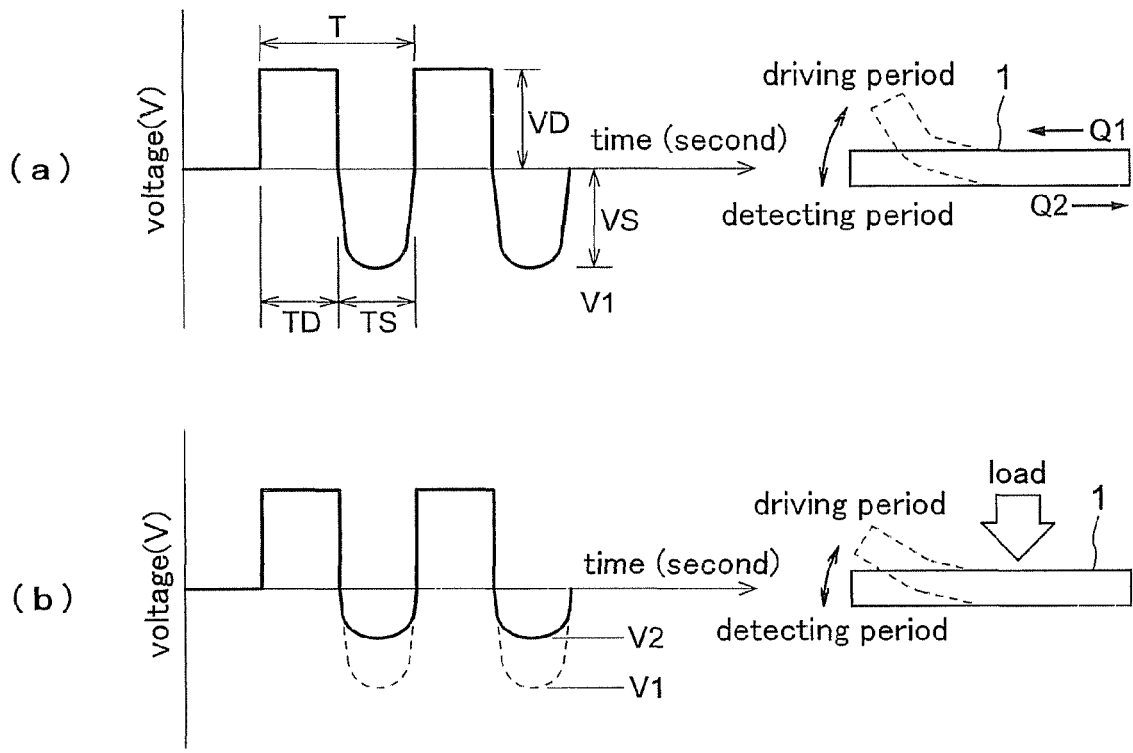
[FIG. 8] an explanatory view schematically illustrating operational principle of the load detecting apparatus according to the invention.
Figure 9:
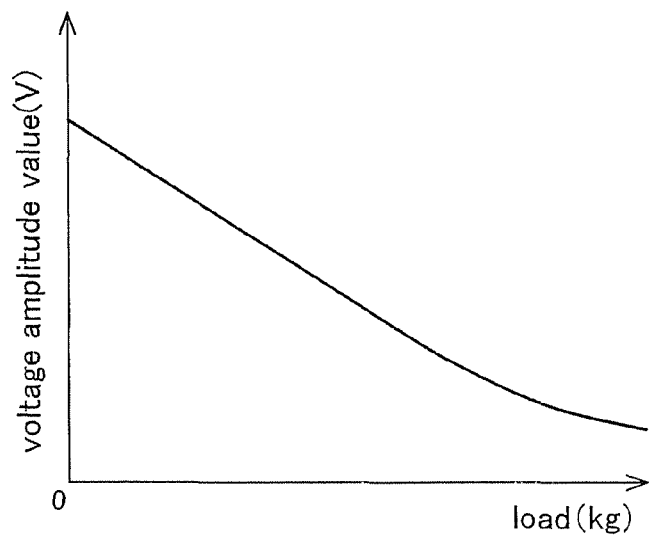
[FIG. 9] a graph schematically illustrating relationship between load applied to a load sensor and an amplitude value of detection signal of the load sensor.
Figure 10:
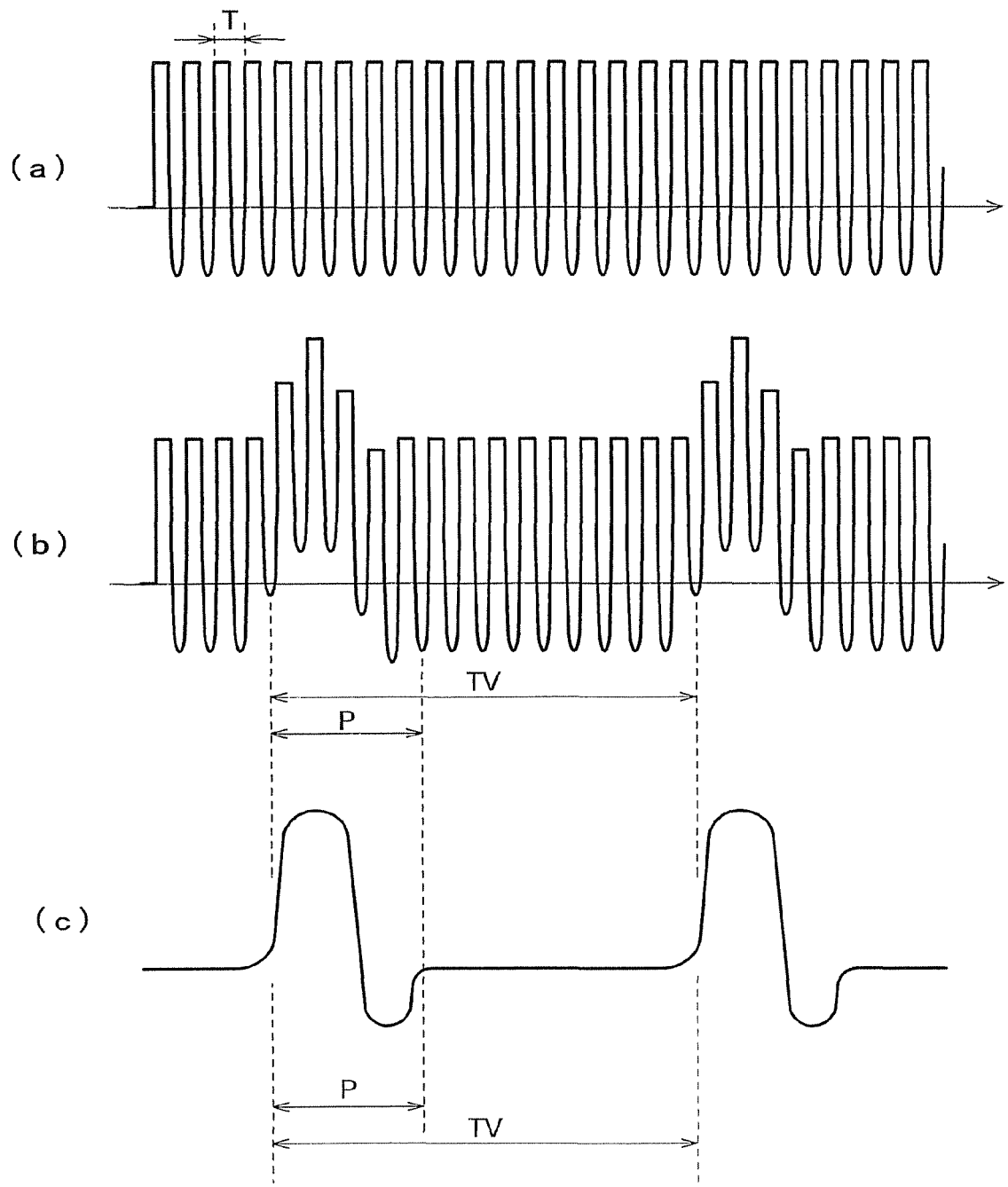
[FIG. 10] a waveform diagram schematically showing another example of input signal to the detecting means shown in FIGS. 1 and 3.
Figure 11:
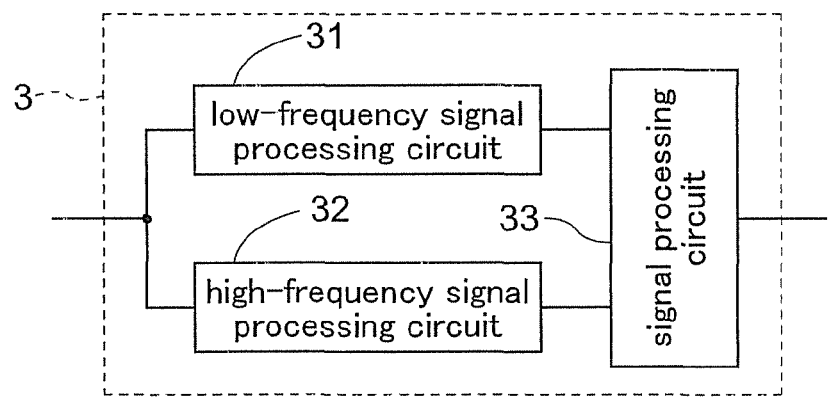
[FIG. 11] a block diagram schematically showing an exemplary construction of a signal processing section shown in FIG. 1.
Figure 12:
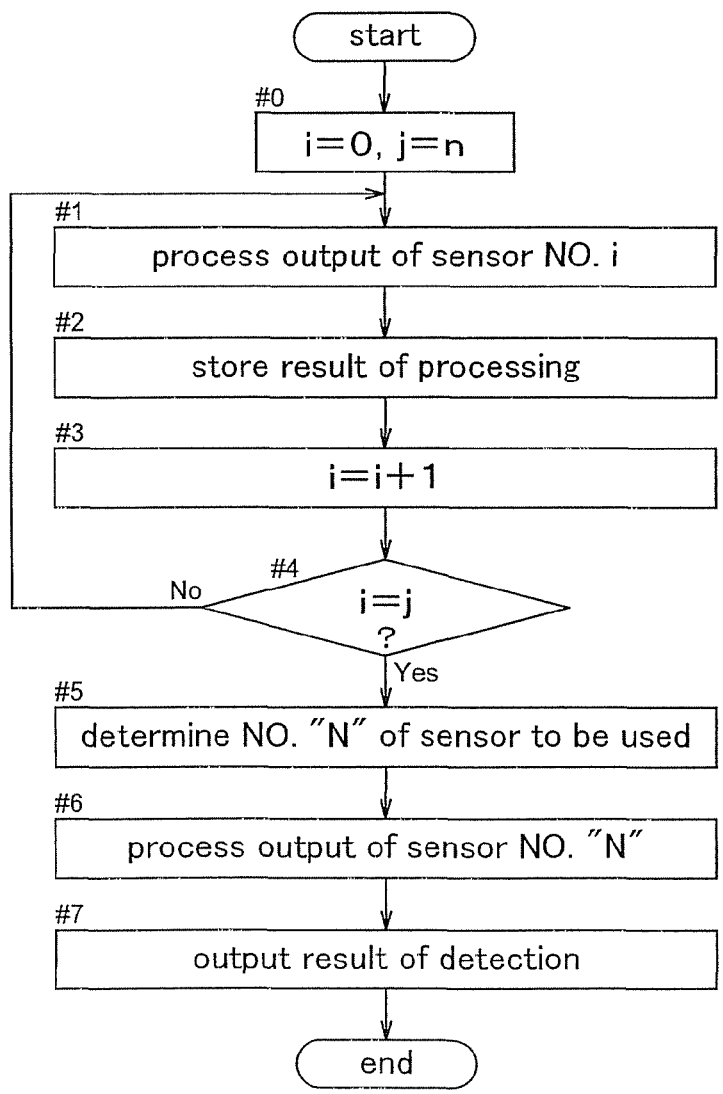
[FIG. 12] a flowchart illustrating processing procedure of the load detecting apparatus relating the embodiment of the present invention.
Figure 13:
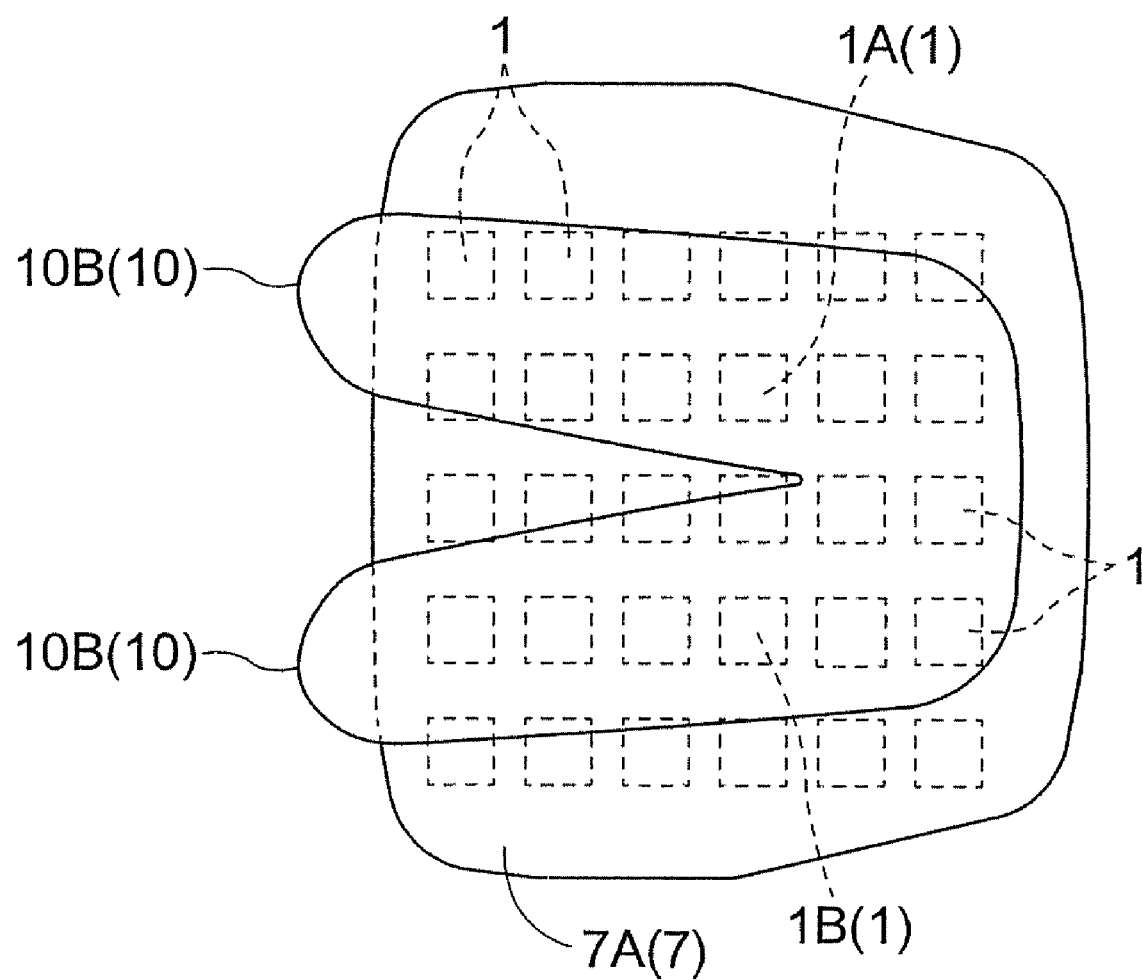
[FIG. 13] an explanatory view showing an example of load sensor selected by the load detecting apparatus shown in FIG. 1.

DESCRIPTION OF REFERENCE MARKS 1. load sensor
3 signal processing section (detecting means)
4 information processing section (detecting means)
5 detecting means
6 selecting means
7 support
S detection signal

The invention claimed is:

1. A load detecting apparatus comprising:
   a plurality of load sensors distributed within a detection target area of a support for supporting a body of a human or an animal;
   driving means for deforming each load sensor to cause each load sensor to issue an output that varies depending on whether or not the load sensor under deformation by the driving means receives a reaction force from the body;
   selecting means configured for obtaining outputs from the plurality of load sensors and subsequently selecting one or some of the plurality of load sensor(s), based on either the outputs from the respective load sensors or the outputs from the respective load sensors, plus disposing positions of the respective load sensors; and
   detecting means capable of detecting load and vibration applied to the support, based on the output(s) from the selected load sensor(s).

2. The load detecting apparatus according to claim 1, wherein said selecting means effects the selection of one or some of the load sensor(s), based on distribution of the outputs from the load sensors relative to the disposing positions thereof.

3. The load detecting apparatus according to claim 1, wherein said selecting means selects one load sensor which has the largest absolute value of the loads indicated by the outputs from the plurality of load sensors.

4. The load detecting apparatus according to claim 1, wherein said selecting means effects the selection of one or some load sensor(s), based on signals having a first frequency range contained in the outputs from the plurality of load sensors, and
   wherein said detecting means effects the detection of the load and the vibration, based on signals having a second frequency range different from said first frequency range, also contained in the output(s) from the selected load sensor(s).

5. The load detecting apparatus according to claim 1, wherein said selecting means effects the selection of the one or some of the load sensor(s), based on signals of a first frequency range included in the outputs of the plurality of load sensors, and
   wherein said detecting means effects the detection of the load and the vibration, based on a signal of a second frequency range different from said first frequency range included in the output(s) from the selected load sensor(s) and a signal of said first frequency range.

6. The load detecting apparatus according to claim 1, wherein said selecting means selects the outputs from the plurality of load sensors one after another, thereby scanning all of the plurality of load sensors present within the detection target area and subsequently selects the one or some of the plurality of load sensor(s), based on either the outputs from the respective load sensors or the outputs from the respective load sensors plus disposing positions of the respective load sensors.

7. The load detecting apparatus according to claim 6, wherein said detecting means includes a signal processing section for signal-processing the outputs from the load sensors and an information processing section for detecting the load and the vibration based on the signal-processed outputs, and
   said selecting means effects selection for the scanning and the selection of the one or some of the plurality of load sensor(s), in accordance with an instruction from said information processing section.

8. The load detecting apparatus according to claim 1, wherein said detection target area comprises an area to contact the human or animal laying or seated thereon;
   said plurality of load sensors comprise piezoelectric sensors for converting a strain or vibration into electric signals by the piezoelectric effect and outputting the electric signals; and
   said detecting means is configured to detect at least one of a weight, pulses, and breathing of the human or animal.

9. The load detecting apparatus according to claim 5, wherein said detection target area comprises an area to contact the human or animal laying or seated thereon;

said plurality of load sensors comprise piezoelectric sensors for converting a strain or vibration into electric signals by the piezoelectric effect and outputting the electric signals;

said selecting means effects the selection of the one or some of the plurality of the load sensor(s), based on signals of the first frequency range outputted from said load sensors in response to application of the weight of the human or the animal; and said detecting means detects the weight of the human or animal based on the signal of the first frequency range and also detects at least one of the pulse and breathing of the human or animal based on the signal of the second frequency range.

10. A load detecting method comprising:

energizing a plurality of load sensors distributed within a detection target area of a support which supports a body of a human or an animal to deform each load sensor and derive from the load sensors an output that varies depending on whether or not each load sensor under deformation by the energizing receives a reaction force from the body;

an evaluating step of obtaining the outputs one after another from the plurality of load sensors;

a selecting step of selecting one or some of the plurality of load sensor(s), based on either the result of said evaluating step or on the result of said evaluating step plus disposing positions of the respective load sensors; and a detecting step of obtaining output of the load sensor(s) selected at said selecting step and detecting one or both of load and vibration applied to the support.

11. A load detecting apparatus comprising:

a support configured to support a human or animal body;

a plurality of load sensors distributed over a detection area of the support;

means for deforming the load sensors which are distributed over the detection area of the support, and each of the load sensors providing an output that varies depending on whether the load sensor deformed by the means for deforming receives a reaction force from the body;

selecting means connected to the load sensors distributed over the detection area of the support to receive the outputs from the load sensors and for selecting at least one of the plurality of load sensors based at least on the output from the load sensor; and detecting means for detecting load and vibration applied to the support using the output from the selected load sensors.

* * * * *